(12) United States Patent
Lapp et al.

(10) Patent No.: US 10,363,408 B2
(45) Date of Patent: *Jul. 30, 2019

(54) SCREW CONNECTOR FOR MEDICAL HOSE SYSTEMS AND MEDICAL HOSE SYSTEMS HAVING A SCREW CONNECTOR

(71) Applicant: Fresenius Medical Care Deutschland GmbH, Bad Homburg (DE)

(72) Inventors: Uwe Lapp, Butzbach (DE); Lothar Leick, Merzig (DE); Ralf Mueller, Bad Homburg (DE); Peter Urban, Oberthal (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 338 days.

This patent is subject to a terminal disclaimer.

(21) Appl. No.: 15/108,326

(22) PCT Filed: Feb. 24, 2015

(86) PCT No.: PCT/EP2015/053789
§ 371 (c)(1),
(2) Date: Jun. 27, 2016

(87) PCT Pub. No.: WO2015/128310
PCT Pub. Date: Sep. 3, 2015

(65) Prior Publication Data
US 2016/0325087 A1    Nov. 10, 2016

(30) Foreign Application Priority Data
Feb. 27, 2014 (DE) .......... 10 2014 002 649

(51) Int. Cl.
*A61M 39/00* (2006.01)
*A61M 39/10* (2006.01)
(Continued)

(52) U.S. Cl.
CPC ...... *A61M 39/1011* (2013.01); *A61M 1/3653* (2013.01); *A61M 39/16* (2013.01);
(Continued)

(58) Field of Classification Search
CPC ............ A61M 1/3653; A61M 39/1011; A61M 39/16; A61M 2039/1033;
(Continued)

(56) References Cited

U.S. PATENT DOCUMENTS 5,650,071 A * 7/1997 Brugger .............. A61M 1/3643
                                                       210/646
5,676,270 A    10/1997 Roberts
(Continued)

FOREIGN PATENT DOCUMENTS

DE      3515665    5/1986
GB      555123     8/1943
(Continued)

*Primary Examiner* — Benjamin J Klein
(74) *Attorney, Agent, or Firm* — Jacobson Holman, PLLC.

(57) ABSTRACT

A screw connector for medical hose systems is configured for catch engagement in a half-open sterilization position. The connector includes a first connecting element having a first lumen and an outside thread, and a second connecting element having a second lumen, and an elastically deformable union nut having an inside thread. The inside thread and the outside thread are configured to be screwed together, with the outside thread having a first formation and the inside thread a second formation, with deformation of the nut via the first formation in a predetermined first angle-of-rotation range without engaging the second formation. The inside thread and the outside thread, and the first formation and the second formation, are configured for catch engagement of the first formation in the second formation when the inside thread and the outside thread are screwed together in
(Continued)

a predetermined second angle-of-rotation range to provide the half-open sterilization position.

15 Claims, 3 Drawing Sheets

(51) Int. Cl.
*A61M 39/16* (2006.01)
*A61M 1/36* (2006.01)
*F16B 39/30* (2006.01)

(52) U.S. Cl.
CPC ............... *A61M 2039/1033* (2013.01); *A61M 2039/1044* (2013.01); *F16B 39/30* (2013.01)

(58) Field of Classification Search
CPC .. A61M 2039/1038; A61M 2039/1044; A61M 2039/1083
See application file for complete search history.

(56) References Cited

U.S. PATENT DOCUMENTS

| | | | |
|---|---|---|---|
| 6,381,928 | B1 | 5/2002 | Gregory |
| 2011/0028913 | A1* | 2/2011 | Muramatsu ........ A61M 5/31511 604/222 |
| 2014/0339811 | A1* | 11/2014 | Wong .................... A61J 1/2096 285/92 |
| 2016/0325086 | A1* | 11/2016 | Lauer ................. A61M 39/1011 |

FOREIGN PATENT DOCUMENTS

| | | |
|---|---|---|
| JP | 2005000466 | 1/2005 |
| WO | WO 96/40320 | 12/1996 |
| WO | WO 99/20376 | 4/1999 |
| WO | WO 2010/121819 | 10/2010 |

\* cited by examiner

SCREW CONNECTOR FOR MEDICAL HOSE SYSTEMS AND MEDICAL HOSE SYSTEMS HAVING A SCREW CONNECTOR

BACKGROUND OF THE INVENTION

1. Field of the Invention

The invention relates to a screw connector for medical hose systems and a medical hose system having a screw connector as well as sterilization of such medical hose systems by steam sterilization and/or gas sterilization. A plurality of connectors for medical hose systems are known, in particular so-called Luer-Lock connectors. Medical hose systems are used in infusion technology and in extracorporeal blood treatment, for example, and must be sterile for these applications.

2. Description of Related Art

To ensure sterility, medical hose systems for infusion technology and for extracorporeal blood treatment are packaged in a suitable closed package in which they are sterilized. The sterilization may be performed as steam sterilization and/or gas sterilization. The aforementioned sterilization methods require that gases and/or hot steam be able to reliably reach all the external and internal surfaces of the medical hose system.

The document DE 35 15 665 C1 discloses a closure stopper for tight sealing of connections in medical technology, in particular Luer-Lock connections. Its two connecting parts optionally permit either a loose attachment, in which it is still possible for gas to pass through, as well as a tight closing of the connection. The loosely attached position and the closed position are separated by a stop, which can be overcome by elastic deformation. It is therefore proposed that the stop be designed with two internal radial ring ribs in front of the internal thread of the closure stopper and two outer wings on the complementary connecting part.

One disadvantage of this known closure stopper is that the two internal radial ring ribs can be overcome only by a compressive force acting axially on the connecting parts individually and one after the other, relative to the axis of rotation of the closure stopper. Canting may occur if the compressive force does not act precisely axially. Consequently, the user must align the connecting parts very accurately, which is made difficult by the fact that the ring ribs are arranged directly in front of the inside thread of the closure stopper.

When applying a force that does not act precisely axially or an axial force that is too low, the closure stopper may fall off, and in the worst case, it might even fall on the ground, so it would no longer be sterile. The known closure stopper is therefore unreliable and complicated to handle.

On the whole, this results in a burden for the clinic personnel due to procedures that are complicated and/or subject to error.

The document WO 99/20376 A1 proposes a method for rinsing a blood hose set for the extracorporeal blood treatment; it is proposed here that the arterial patient connector and the venous patient connector be connected to a connector already during the production of the blood hose set and then be sterilized in this connected form.

The document WO 96/40320 A1 proposes another method for rinsing a blood hose set for the extracorporeal blood treatment, wherein it is proposed that the arterial patient connector and the venous patient connector be connected by a Y-connector with a drain when rinsing the blood hose set. It is therefore proposed that the packaged extracorporeal blood hose set already contain the Y-connector connected to the arterial patient connector and the venous patient connector.

The document WO 2010/121819 A1 by the present applicant of the present patent application discloses a blood cassette having a blood hose set for the extracorporeal blood treatment with an arterial patient line and a venous patient line. In addition, the document WO 2010/121819 A1 also discloses a method for rinsing an extracorporeal blood circuit, wherein the patient connectors of the arterial patient line and the venous patient line are connected to the rinse line of the dialysis machine by means of a T-connector. Reference is made to the contents of the document WO 2010/121819 A1 fully in the present patent application.

Conical connectors with a 6% (Luer) cone are known for syringes, cannulas and certain other medical devices, in particular lockable conical connectors, which are also referred to as Luer-Lock connectors.

SUMMARY OF THE INVENTION

Therefore one object of the present invention is to overcome at least one of the aforementioned disadvantages and to provide an improved screw connector for medical hose systems.

This object is achieved with the features of the invention as described herein. Advantageous embodiments of the invention are also as described herein.

The present invention makes available a screw connector for a medical hose system, having at least one first connecting element with a first lumen and an outside thread and at least one second connecting element with a second lumen and an elastically deformable union nut having an inside thread. The inside thread and the outside thread are configured to be screwed to one another, wherein the outside thread has at least one first formation and the inside thread has at least one second formation. The inside thread and the outside thread are configured for mutual screw connection with elastic deformation of the union nut by means of the first formation in at least one predetermined first angle-of-rotation range without the first formation engaging in the second formation. The inside thread and the outside thread as well as the first formation and the second formation are configured for lock engagement of the first formation in the second formation when the inside thread and the outside thread are screwed together in a predefined second angle-of-rotation range.

The first connecting element and the second connecting element are each advantageously configured to be gas-permeable between an outer environment of the screw connector and the interior of the screw connector, which is formed at least by the first lumen when the inside thread is screwed together with the outside thread in the second angle-of-rotation range; this condition is referred to below as the half-open sterilization position.

The term "screw connector" is not limited to a certain embodiment of the fluid-tight connection of a first lumen with a second lumen in conjunction with the present invention. The fluid-tight connection in particular through sealing surfaces may be independent of the screw connection and/or may exist in addition to the screw connection. The screw connection may comprise in particular an additional securing means and/or locking means of a fluid-tight connection of a first lumen with a second lumen to prevent unintentional loosening.

A half-open sterilization position may be understood in many embodiments to mean that the two complementary halves of a Luer-Lock connector are not connected to form a seal but instead a definite gap is set between the complimentary conical faces of the Luer-Lock connector. In steam sterilization and/or gas sterilization, the vapor and/or the gas can therefore also penetrate through the gap between the complementary halves and into the respective interior of the complementary halves of the Luer-Lock connector. The term "half-open" is used to show clearly that the two complementary halves of the Luer-Lock connector are each at least partially covered by the complementary half of the Luer-Lock connector. This has the advantage that, despite the defined gap, a touch protection is ensured for both complementary halves of the Luer connector without requiring additional touch protection caps to do so.

In many embodiments, the half-open sterilization position may have the advantage that the two complementary halves of the Luer-Lock connector are already preassembled and need only be connected with a seal for use and secured by tightening the screws. Such embodiments are particularly user-friendly because the operation of connecting the Luer connector is facilitated for the user and/or the user is at least partially relieved of this task.

In one embodiment, the first connecting element and the second connecting element are each designed as complementary halves of a common Luer-Lock connector. The inside thread and the outside thread are each designed as complementary threads of the Luer-Lock connector and serve as additional means of securing the Luer cone to prevent unintentional loosening. The complementary threads of the Luer-Lock connector are designed to be compatible at least with regard to thread shape, thread diameter, thread pitch and thread length and thus are configured and provided for mutual screw connection.

In one embodiment of the screw connection, the first lumen is designed as a female half of the Luer connector and the second lumen is designed as the male half of the Luer connector.

The threaded nut of the screw connector is preferably compatible with the complementary halves of standardized connectors because the second formation on the thread flanks of the inside thread of the threaded nut does not have an interfering effect with respect to the complementary halves of standardized connectors so that, for example, the screw connection of standardized Luer-Lock connectors on the hose line sections of dialysis needles, cannulas, catheters or on ports with the threaded nut according to the invention is not impaired.

The outside thread preferably has a first formation, which is a local elevation on the core diameter of the outside thread between two neighboring thread flanks. This yields an enlarged core diameter of the outside thread in the region of the elevation locally.

The inside thread preferably has a second formation, which is a local clearance on the thread flank of the inside thread.

In one embodiment, the local clearance is a groove running substantially in the axial direction of the inside thread in a thread flank of the inside thread and the local elevation is designed as a rib running substantially in the axial direction of the outside thread between two neighboring thread flanks of the outside thread.

In another embodiment, the first formation comprises multiple local elevations spaced a distance apart from one another on the core diameter of the outside thread between two neighboring thread flanks. The core diameter of the outside thread is then enlarged in the area of each of the local elevations. The inside thread preferably has several second formations which are local clearances on the thread flank of the inside thread. The number of local elevations may correspond to the number of local clearances.

In accordance with the teaching of the present invention, the nut is configured for elastic deformation due to the first formation in a predetermined first angle-of-rotation range in which the first formation does not engage in the second formation. The diameter of the nut can therefore be widened elastically with rotation in a first angle-of-rotation range if a rib running substantially in the axial direction of the outside thread slides along the thread flank and/or presses the thread flank of the inside thread of the nut between two neighboring thread flanks of the outside thread in the interior of the nut.

In other words, in the predetermined first angle-of-rotation range, the first formation does not encounter a second formation, so that the first formation cannot engage in a second formation in the predetermined first angle-of-rotation range.

The inside thread and the outside thread as well as the first formation and the second formation are additionally configured for engagement of the first formation in the second formation when the inside thread and the outside thread are screwed together at a predetermined second angle-of-rotation range.

For example, in one embodiment, a rib running substantially in the axial direction of the outside thread engages in a groove in the thread flank of the inside thread, said groove running substantially in the axial direction of the inside thread between two neighboring thread flanks of the outside thread, when the inside thread and the outside thread are screwed together in the predetermined second angle-of-rotation range.

The second angle-of-rotation range may be determined by the shape and the arrangement of the first and/or second formations. In many embodiments, the second angle range may be defined essentially by the width of the first formation and the width of the second formation in the direction of rotation of the thread. The second formation may be somewhat larger in comparison with the first formation, which thus results in play. This play may facilitate the catch engagement of the first formation in the second formation.

In another embodiment, the second connecting element may have a sealing cap with a sealing structure or may be a sealing cap with a sealing structure. Such an embodiment may occur, for example, when the second connecting element is configured as a touch protection cap and/or as a closing cap. The sealing structure may be configured for airtight and/or fluid-tight sealing with a first connecting element.

In another embodiment, the second connecting element has a lumen which is also referred to as the second lumen, and the nut is configured as a union nut. The union nut is rotatably mounted on the second connecting element so that the union nut can be screw-connected to a first connecting element without causing rotation of the second connecting element. Such an embodiment is especially advantageous when the screw connector according to the invention is provided for connecting two hose line sections which should not rotate in screw connection of the screw connector.

It is also advantageous that a screw connector for medical hose systems is made available, allowing a half-open sterilization position and at the same time being ergonomic and reliable in handling. The half-open sterilization position is reliable and secure at the same time.

In another embodiment, the screw connector is configured to be screwed in an airtight and/or fluid-tight manner in another angle-of-rotation range. The first connecting element and the second connecting element are each configured to be gas-permeable between an outer environment of the screw connector and an interior of the screw connector formed at least by the first lumen in screw connection of the inside thread with the outside thread in the second angle-of-rotation range, and also the first connecting element and the second connecting element are each configured to form an airtight and/or fluid-tight seal between the outer environment of the screw connector and the interior of the screw connector in screw connection of the inside thread with the outside thread in the wider angle-of-rotation range. For screw connection in the wider angle-of-rotation range, it is first necessary to exceed the second angle-of-rotation range. In other words, the screw connector is tightened further beyond the second angle-of-rotation range. In doing so the first formation first disengages from the second formation. For the disengagement of the first formation from the second formation, a torque must be applied to the nut. The airtight and/or fluid-tight position is reached only by completely tightening the screw connection.

In accordance with the teaching of the present invention, the first connecting element and the second connecting element may each be configured to set a half-open sterilization position of the screw connector for a gas sterilization and/or steam sterilization of the medical hose system in screwing of the inside thread with the outside thread in the at least one predefined second angle-of-rotation range. The half-open sterilization position is set by securing the position of the inside thread relative to the outside thread in the second angle-of-rotation range, such that in this position there is a gap between the first lumen and the second lumen, so that gas and/or steam can penetrate into the interior of the first lumen and/or of the second lumen. This securing is achieved because the first formation engages in the second formation in the at least one predetermined second angle-of-rotation range. An unintentional change in the half-open sterilization position can thus be reliably prevented.

In another embodiment, the screw connector is part of a medical hose system. In the present invention, the term "medical hose system" comprises all medical products which have at least one hose section and in particular are configured and/or provided for the extracorporeal blood treatment, in particular for hemodialysis, hemofiltration or hemodiafiltration or for peritoneal dialysis or for infusion of medical solutions into the patient.

One embodiment of the medical hose system according to the invention is a blood hose set for the extracorporeal blood treatment with an arterial patient hose and a venous patient hose, wherein at least the patient's end of the venous patient hose and/or the patient's end of the arterial patient hose is designed as the first connecting element or the second connecting element of the screw connector according to the invention.

In one embodiment, a preconnected blood hose set is made available for the extracorporeal blood treatment with a three-way connector, which permits a half-open sterilization position of the Luer-Lock connections of the arterial and venous patient connectors preconnected to the three-way connector for sterilization of the blood hose set. The three-way connector has three connections to three connected lumens. At least one connection of the three-way connector is designed as the first connecting element, in particular as the female half of the Luer-Lock connector and at least the patient's end of the venous patient hose and/or the patient's end of the arterial patient hose is/are designed as the second connecting element of the screw connector according to the invention, in particular as the male half of the Luer-Lock connector. At least two connections of the three-way connector are especially preferably designed as the first connecting element, in particular as the female half of a Luer-Lock connector and both the patient's end of the venous patient hose as well as the patient's end of the arterial patient hose are designed as the second connecting element of the screw connector according to the invention, in particular as the male half of the Luer-Lock connector. This yields the additional advantage that at least two closing caps for closing the patient's end of the venous patient hose and for closing the patient's end of the arterial patient hose can be eliminated because this function is fulfilled by the three-way connector. The third connection of the three-way connector can be sealed with a conventional covering cap or may also be equipped with a screw connector, wherein the screw connector is then preferably designed as a sealing cap. The medical hose system is thus configured for short-circuiting the patient's end of the arterial patient hose and the patient's end of the venous patient hose with the three-way connector. This has the advantage that, after completely tightening the Luer-Lock connector by means of the third connection, the medical hose system can be connected to a source for medical priming fluid by means of the third connection and can be filled and rinsed with the medical priming fluid. The medical hose system is thus preconnected for the purpose of rinsing with medical priming fluid, which thus makes handling more practical.

A preconnected blood hose set is thus advantageously made available in the form of a three-way connector for the extracorporeal blood treatment; this connector permits a half-open sterilization position of the Luer-Lock connections of the arterial and venous patient connectors preconnected to the three-way connector for sterilizing the blood hose set and at the same time is ergonomic and reliable in handling. This yields the additional advantage that it eliminates at least two closing caps for closing the arterial patient connector and the venous patient connector.

In one embodiment, the medical hose system has a blood cassette for the extracorporeal blood treatment, wherein the end of the arterial patient hose opposite the patient's end of the arterial patient hose and the end of the venous patient hose opposite the patient's end of the venous patient hose are each connected to the blood cassette for the extracorporeal blood treatment. The blood cassette may include additional elements of an extracorporeal blood circulation, for example, selected from air bubble separators, clot filters, ports, cavities and lines for receiving and/or carrying blood and/or medical fluids as well as valves and pump elements. In such an embodiment, ports of the blood cassette and additional hose line sections on the blood cassette may also be equipped with a screw connector according to the invention, wherein the screw connector is then preferably designed as a closing cap.

In one embodiment, the medical hose system is packaged in sterile form in a dosed wrapping, wherein the patient's end of the arterial patient hose and the patient's end of the venous patient hose are connected to a three-way connector in the half-open sterilization position.

In accordance with the teaching of the present invention, the hose connector is suitable and is provided for use for gas sterilization and/or steam sterilization of a medical hose system.

The inventors of the present invention have recognized that the complementary halves of a screw connector of a medical hose set, which deviates from the standard, should be usable not only with restriction but preferably as flexibly as possible, in particular to be compatible with use in the clinic.

In a certain embodiment of the screw connector, the second connecting element is compatible with a mating piece of a standardized Luer-Lock connector for fluid-tight screw connection because the second formation cannot have an interfering effect here. The use of the screw connector according to the invention in sterilizing a medical hose set therefore hardly restricts the use of the medical hose set in the clinic. The second connecting element can therefore be used in a compatible and therefore flexible manner in the clinic operation. Dialysis needles which have a short hose section with a female half of a standardized Luer-Lock connector are mentioned as one example. These can be connected without restriction to the second connecting element of a screw connector according to the invention and are provided for such connection. The second connecting element of the screw connector according to the invention, which can be provided on the patient's end of the venous patient hose and the patient's end of the arterial patient hose, can be connected to the dialysis needle, which has a female half of a standardized Luer-Lock connector.

The screw connector is preferably insensitive to axial pressure or tension on the first and/or second connecting element when the inside thread is screwed to the outside thread. The screw connector is then robust with respect to the unintended disconnection due to tensile and/or bending stresses on the connecting parts, which may occur in packaging, storage and shipping, because the thread flanks absorb the tensile and bending forces. Release is possible only by targeted rotational movement beyond the resistance.

The elastic deformation of the nut or the union nut in screw connection in the first angle-of-rotation range preferably amounts to 0.15 to 0.25 millimeter, in particular on standardized lockable Luer connections and corresponds to the excess between the first formation and the inside thread.

In one embodiment, the screw connector may be configured for only a single catch engagement of the first formation in the second formation. Repeated catch engagement is not provided in such embodiments because the first formation and/or the second formation become worn out on catch engagement and screw connection beyond the catch engagement. Such embodiments are especially inexpensive because of the low demands of the stability of the first formation and/or the second formation.

In one embodiment of the screw connector, a guide aid and/or guide distance is provided, which facilitates handling by the user in the clinic and also permits assembly by robots. The guide aid may be implemented by the thread itself in many embodiments.

Thus a screw connector, which is ergonomic and reliable to handle, is advantageously made available.

The halves of the screw connector may thus be guided securely and held in manual screwing and loosening in the clinic, which is especially advantageous when the screw connector is made up of small parts. The outside diameter of the nut of the screw connector according to the invention may amount to, for example, 6 millimeters to 12 millimeters or 12 millimeters to 25 millimeters.

Manual screwing and/or loosening of the screw connector by turning the nut or the unit nut of the second connecting element is/are typically accomplished between the fingertips of the user's thumb and index finger, on one hand, while the first connecting element is held securely by the fingers of the other hand. In tightening and/or loosening the screw connector, the user first senses from the beginning that the first connecting element is rotated by an angle of rotation with respect to the second connecting element and is reliably guided by the thread. Secondly, the user senses an altered resistance in this turning depending on the angle of rotation, for example, for the first time when the nut or union nut is turned with its elastic deformation due to the first formation in the predetermined first angle-of-rotation range without the first formation engaging in the second formation, and secondly, when the first formation engages in the second formation, when the inside thread and the outside thread are screwed together in a predefined second angle-of-rotation range. In addition, the user can sense an altered resistance in turning the connector when the inside thread and the outside thread are screwed together beyond the predetermined second angle-of-rotation range and are tightened until fluid-tight. The user can sense these altered resistances even in unscrewing the connectors until the first connecting element is separated from the second connecting element. When the screw connector has a plurality of catch engagement positions, the user can sense the variable resistances at each catch engagement position.

The screw connector thus permits tactile feedback in manual handling of the screw connector according to the invention due to the torsional resistance, which depends on the rotational angle, in other words, imparting the sensation of tactility of progress when handling with the fingers. The distance between the unlocked state and the locked state, lengthened by the thread and vice versa is advantageous here.

Thus a screw connector, which is also ergonomic and reliable in handling, is advantageously made available.

The nut or the union nut of the second connecting element may be configured by the choice of a suitable elastic material and the shaping for elastic deformation by the first formation of the first connecting element.

Plastics, for example, have proven suitable as the material for the first and second connecting elements.

In many embodiments, PP (polypropylene) in particular is a suitable material for the first and second connecting elements.

BRIEF DESCRIPTION OF THE DRAWINGS

One exemplary embodiment according to the present teaching is described below with reference to the drawings. On the basis of the exemplary embodiment depicted in the drawings, additional details and advantages are described further. The reference numerals in the figures have the same meanings in all the figures.

They show.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
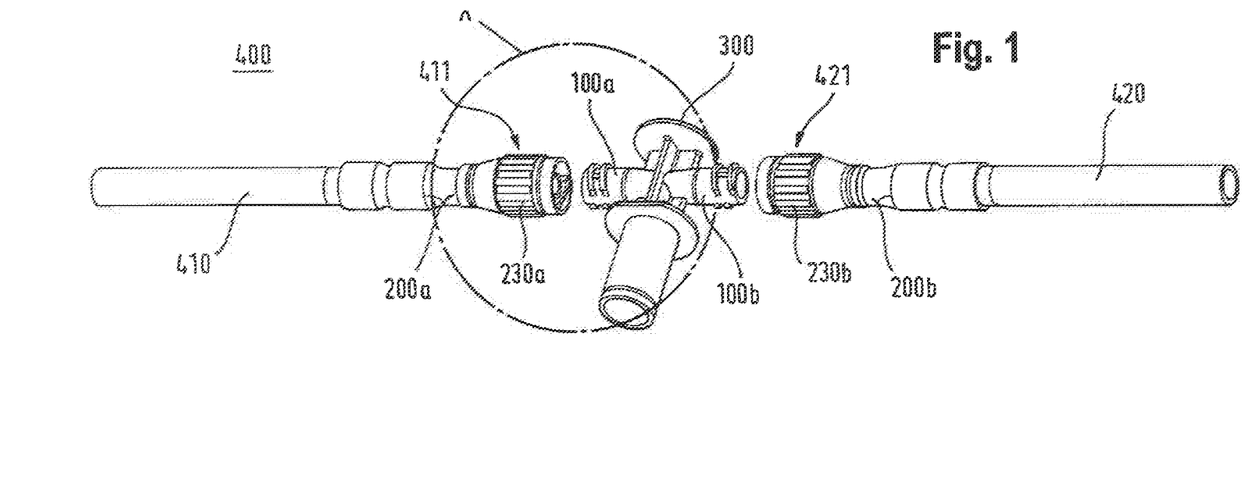
FIG. 1 shows a view of a section of a medical blood hose set.

FIG. 1 shows a view of a section of a medical hose system, preferably a medical blood hose set, having an arterial patient line (410) with a patient's end (411) and a venous patient line (420) with a patient's end (421) as well as a three-way connector (300), wherein the arterial patient line (410) and the venous patient line (420) are not connected to the three-way connector (300). The three-way connector (300) has two connections which are designed as a first connecting element (100a, 100b) of a screw connector. The first connecting element (100a, 100b) is preferably designed as the female half of Luer-Lock connector. The patient's end (421) of the venous patient line (420) and the patient's end (411) of the arterial patient line (410) are each designed as the second connecting element (200) of the screw connector. The second connecting element (200a, 200b) of each is designed as the male half of the Luer-Lock connector and has a union nut (230a, 230b), which is designed for screw connection to the female half of the Luer-Lock connector.

Figure 3:
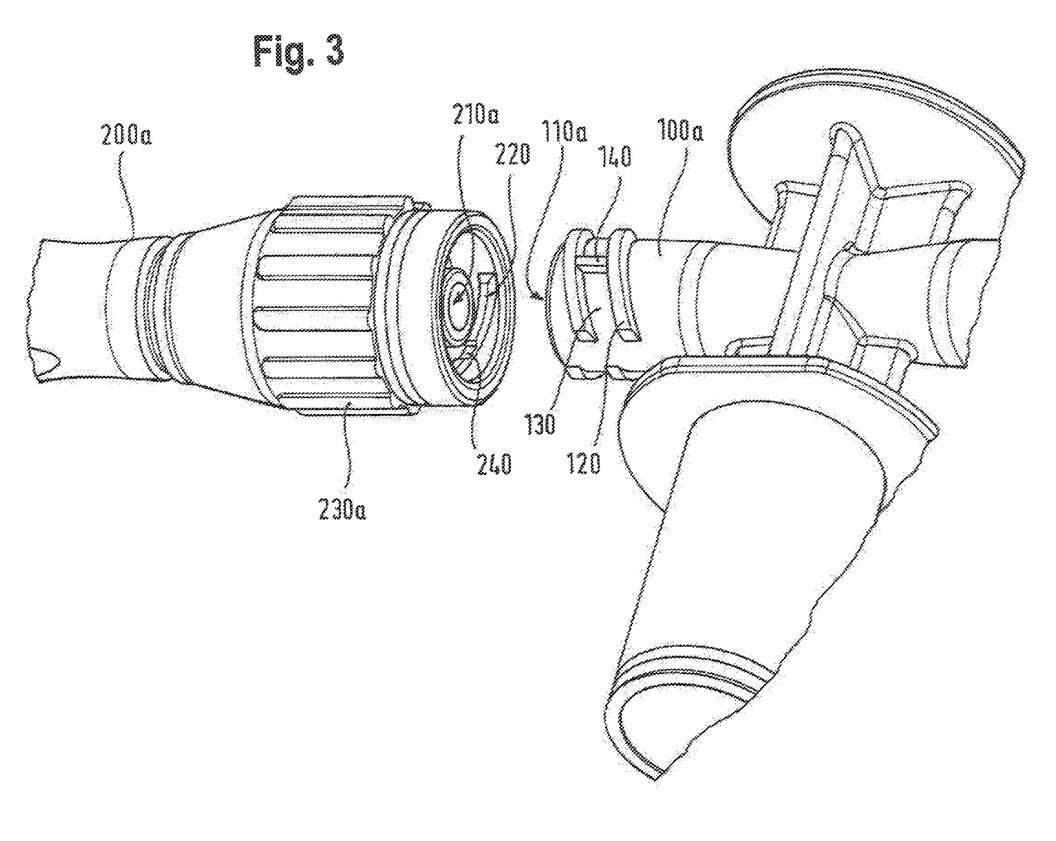
FIG. 3 shows a detailed diagram X from the section of a medical hose set according to FIG. 1.

FIG. 1 additionally shows a region X characterized by a dash-dot line, shown as an enlarged detail in FIG. 3.

Figure 2:
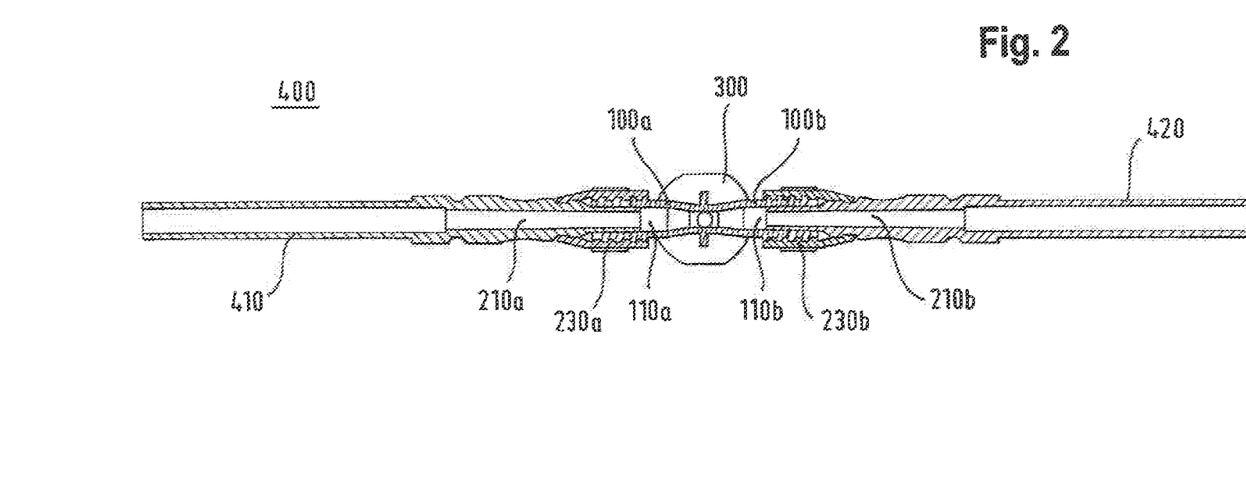
FIG. 2 shows a sectional diagram of the section of a medical blood hose set according to FIG. 1.

FIG. 2 shows a sectional diagram of the section of a medical blood hose set from FIG. 1, wherein the arterial patient line (410) and the venous patient line (420) are each connected to the three-way connector (300) in FIG. 2. The sectional diagram shows that three-way connector (300) has first connecting elements (100a, 100b) and first lumens (110a, 110b). The first connecting elements (100a, 100b) are each designed as the female half of the Luer-Lock connector.

The patient end (421) of the venous patient line (420) and the patient's end (411) of the arterial patient line (410) are each designed as the second connecting element (200a, 200b) with a second lumen (210a, 210b). The second connecting element (200a, 200b) is preferably designed as the male half of the Luer-Lock connector in each case and each as a union nut (230a, 230b), each being screw-connected to the complementary female half of the Luer-Lock connector.

The inside thread and the outside thread are each designed as complementary threads of the Luer-Lock connector. The complementary thread of the Luer-Lock connector are designed to be compatible at least with regard to the thread shape, thread diameter, thread pitch and thread length and thus are configured and provided for mutual screw connection.

FIG. 3 shows the detail drawing X of the view of the section of a medical blood hose set according to FIG. 1. The description of the screw connector is applicable to the left screw connector (200a, 230a, 100a), shown in the detail drawing X, for example, from FIG. 1, but it also applies equally to the right screw connector (200b, 230b, 100b) from FIG. 1, which is not shown in detail.

The detail drawing X shows an enlarged view of the patient's end (411) of the arterial line (410) with the second connecting element (200a) having the union nut (230a). The detail drawing shows the mouth of the second lumen (210a) and a section of the inside thread (220) in the region of the open end of the union nut (230a). The inside thread (220) has the second formation (240). The second formation (240) is preferably designed as a groove running substantially in the axial direction of the inside thread in the thread flank of the inside thread (220). The first connecting element (100a) with the lumen (110a) has the outside thread (120), with the thread base (130) and the first formation (140). The first formation (140) is preferably designed as a rib running substantially between two neighboring thread flanks of the outside thread in the axial direction of the outside thread. The rib running substantially in the axial direction of the outside thread thus forms a local elevation on the thread base (130) of the outside thread (120).

The second lumen (210a) is designed to engage in the first lumen (110a) when the Luer-Lock connector is screw-connected. The second connecting element (200a) is therefore designed as the male half of the Luer-Lock connector, and the first connecting element (100a) is designed as the female half of the Luer-Lock connector.

The union nut (230) is preferably made of plastic, in particular polypropylene (PP) and is therefore configured for elastic deformation by means of the first formation (140) in a predetermined first angle-of-rotation range in which the first formation (140) does not engage in the second formation (240). The diameter of the union nut (230) may therefore be widened elastically when twisted into a first angle-of-rotation range when the rib, which runs substantially in the axial direction of the outside thread between two neighboring thread flanks of the outside thread (120) in the interior of the nut, is pressed against the thread flank of the inside thread (220) of the union nut (230) and/or slides along the thread flank of the inside thread (220). The first formation (140) therefore does not reach the second formation (240) in the predetermined first angle-of-rotation range, so that the first formation (140) cannot engage in the second formation (240) in the predetermined first angle-of-rotation range. The inside thread (220) and the outside thread (120) as well as the first formation (140) and the second formation (240) are each configured for catch engagement of the first formation (140) in the second formation (240) when the inside thread (220) and the outside thread (120) are screwed together in a predetermined second angle-of-rotation range. The screw connection status in the second angle-of-rotation range establishes the half-open sterilization position of the screw connector for gas sterilization and/or steam sterilization of the medical hose system. The half-open sterilization position is set by securing the position of the inside thread (220) relative to the outside thread (120) in the first angle-of-rotation range, wherein in this position between the first lumen and the second lumen, there is a gap, so that gas and/or steam can penetrate into the interior of the first lumen and of the second lumen. The fixation is achieved by the fact that the first formation (140) engages in the second formation (240). Thus an unintended change in the half-open sterilization position is reliably prevented, so that the gap remains reliably set.

The screw connector is designed for being screwed in an airtight and/or fluid-tight connection. For a screw connection in the third angle-of-rotation range, it is first necessary to exceed the second angle-of-rotation range, wherein the screw connector is tightened further beyond the second angle-of-rotation range. In doing so the first formation (140) first disengages from the second formation (240). For disengagement of the first formation (140) from the second formation (240), a torque must be applied to the nut. The airtight and/or fluid-tight position is achieved only by completely tightening the screw connection. The complete tightening of the screw connector is advantageously accomplished manually after removing the sterile medical hose system from the dosed sterile wrapping. As soon as the medical screw connector has been tightened to an airtight and fluid-tight connection, the third connection of the three-way connector may be connected to a source for a medical priming fluid to fill the medical hose system with medical priming fluid and rinse it.

The medical hose system according to the exemplary embodiment has a blood cassette for the extracorporeal blood treatment, wherein the end of the arterial patient hose opposite the patient's end of the arterial patient hose and the end of the venous patient hose opposite the patient's end of the venous patient hose are each connected to the blood cassette for the extracorporeal blood treatment (not shown in FIGS. 1 to 3).

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

LIST OF REFERENCE NUMERALS

| Reference numeral | Name |
| --- | --- |
| 100, 100a, 100b | first connecting element |
| 110, 110a, 110b | first lumen |
| 120 | outside thread |
| 130 | base of thread |
| 140 | first formation |
| 200, 200a, 200b | second connecting element |
| 210, 210a, 210b | second lumen |
| 220 | inside thread |
| 230, 230a, 230b | union nut |
| 240 | second formation |
| 300 | three-way connector |
| 400 | medical hose set |
| 410 | arterial patient line |
| 411 | patient's end of the arterial patient line |
| 420 | venous patient line |
| 421 | patient's end of the venous patient line |

What is claimed is:

1. A screw connector for a medical hose system, comprising
at least one connecting element having a first lumen and an outside thread and
at least one second connecting element having a second lumen and an elastically deformable union nut having an inside thread,
the inside thread and the outside thread being configured to be screwed to one another,
with the outside thread having at least one first formation and the inside thread having at least one second formation, and
the inside thread and the outside thread being configured for mutual screw connection with elastic deformation of the union nut via the first formation in at least one predetermined first angle-of-rotation range without the first formation engaging in the second formation, and
the inside thread and the outside thread and the first formation and the second formation being configured for catch engagement of the first formation in the second formation when the inside thread and the outside thread are screwed together in a predetermined second angle-of-rotation range to establish a half-open sterilization position, which provides for gas permeability between an outer environment of the screw connector and an interior of the screw connector.

2. The screw connector according to claim 1, wherein the first connecting element and the second connecting element are each configured as complementary halves of a Luer-Lock connector.

3. The screw connector according to claim 2, wherein the first lumen is configured as a female half of the Luer-Lock connector, and the second lumen is configured as a male half of the Luer-Lock connector.

4. The screw connector according to claim 1, wherein the first formation is a local elevation on a core diameter of the outside thread between two adjacent thread flanks, and the second formation is a local clearance on a thread flank of the inside thread.

5. The screw connector according to claim 4, wherein the local clearance is configured as a groove running substantially in an axial direction of the inside thread in the thread flank of the inside thread, and the local elevation is configured as a rib running substantially between the two adjacent thread flanks of the outside thread in an axial direction of the outside thread.

6. The screw connector according to claim 1, wherein the first connecting element and the second connecting element are each configured to provide the gas permeability between the outer environment of the screw connector and the interior of the screw connector formed by the first lumen and the second lumen in the at least one predetermined second angle-of-rotation range in screw connection of the inside thread with the outside thread, and
the first connecting element and second connecting element are each configured to form a gas-tight and/or a liquid-tight connection between the outer environment of the screw connector and the interior of the screw connector when the inside thread is screwed together with the outside thread in a wider angle-of-rotation range.

7. The screw connector according to claim 6, wherein the first connecting element and the second connecting element are each configured to establish the half-open sterilization position of the screw connector for a gas sterilization and/or a steam sterilization of the medical hose system in screw connection of the inside thread to the outside thread in the at least one predetermined second angle-of-rotation range.

8. A medical hose system having a screw connector according to claim 1, wherein the medical hose system includes a blood hose set for an extracorporeal blood treatment, with the blood hose set having an arterial patient hose and a venous patient hose, and with a patient end of the arterial patient hose and a patient end of the venous patient hose each being configured as the second connecting element.

9. The medical hose system according to claim 8, wherein the medical hose system includes a three-way connector with three connected lumens, with at least two of the three connected lumens being configured as the first connecting element.

10. The medical hose system according to claim 9, wherein the medical hose system is configured for short-circuiting the patient end of the arterial patient hose and the patient end of the venous patient hose with the three-way connector.

11. The medical hose system according to claim 9, wherein the end of the arterial patient hose opposite the patient end of the arterial patient hose, and the end of the venous patient hose opposite the patient end of the venous patient hose, are each connected to a blood cassette for the extracorporeal blood treatment.

12. The medical hose system according to claim 11, wherein the medical hose system is packaged in a closed sterile wrapping, and the patient end of the arterial patient hose and the patient end of the venous patient hose are connected to the three-way connector in the half-open sterilization position.

13. The screw connector according to claim 1, wherein the gas permeability between the outer environment of the screw connector and the interior of the screw connector facilitates a gas sterilization and/or a steam sterilization of a medical hose system associate with an extracorporeal blood treatment, with the medical hose system including a blood hose set having an arterial patient hose and a venous patient hose, and with a patient end of the arterial patient hose and a patient end of the venous patent hose each being configured as the second connecting element.

14. A threaded connector that facilitates a sterilization of a tubing system, said threaded connector comprising:
   a first connecting element that includes a first lumen and an outside thread having a first formation; and
   a second connecting element that includes a second lumen and an elastically deformable union nut with an inside thread having a second formation,
   the outside thread and the inside thread being configured for a first threaded connection with elastic deformation of the union nut via the first formation in a predetermined first angle-of-rotation rang without the first formation engaging the second formation, and
   the outside thread and the inside thread, and the first formation and the second formation, being configured for non-tightened engagement of the first formation in the second formation in a second threaded connection in a predetermined second angle-of-rotation range to establish a half-open sterilization position,
   the half-open sterilization position providing for gas permeability between an outer environment of the threaded connector and an interior of the threaded connector, and the sterilization of the tubing system.

15. The threaded connector according to claim 14, wherein the gas permeability of the half-open sterilization position is provided by a gap between the first lumen and the second lumen.

* * * * *